United States Patent [19]

Maxwell

[11] Patent Number: 4,760,734
[45] Date of Patent: Aug. 2, 1988

[54] APPARATUS FOR MEASURING THE RHEOLOGICAL PROPERTIES OF MATERIALS

[76] Inventor: Bryce Maxwell, 19 McCosh Cir., Princeton, N.J. 08540

[21] Appl. No.: 944,296

[22] Filed: Dec. 19, 1986

Related U.S. Application Data

[63] Continuation-in-part of Ser. No. 826,955, Feb. 7, 1986, abandoned.

[51] Int. Cl.$^4$ .............................................. G01N 3/24
[52] U.S. Cl. ......................................... 73/60; 73/843
[58] Field of Search .................... 73/54, 59, 60, 843; 384/242, 228

[56] References Cited

U.S. PATENT DOCUMENTS

| | | | |
|---|---|---|---|
| 2,484,761 | 10/1949 | Stock | 73/843 |
| 3,277,700 | 10/1966 | Myerholtz et al. | 73/843 |
| 3,479,858 | 11/1969 | Umeno et al. | 338/180 |
| 3,545,257 | 12/1970 | Zemp et al. | 73/59 |
| 3,680,366 | 8/1972 | Moser et al. | 73/800 |
| 4,092,849 | 6/1978 | Maxwell | 73/843 |
| 4,524,611 | 6/1985 | Richon et al. | 73/59 |
| 4,566,324 | 1/1986 | Vinogradov et al. | 73/60 |

FOREIGN PATENT DOCUMENTS

| | | | |
|---|---|---|---|
| 8600408 | 1/1986 | World Int. Prop. O. | 73/59 |
| 1244408 | 9/1971 | United Kingdom | 73/59 |
| 277391 | 5/1971 | U.S.S.R. | 73/59 |
| 1111072 | 8/1974 | U.S.S.R. | 73/59 |
| 787955 | 12/1980 | U.S.S.R. | 73/54 |
| 1062565 | 12/1983 | U.S.S.R. | 73/59 |

Primary Examiner—Stewart J. Levy
Assistant Examiner—Hezron E. Williams
Attorney, Agent, or Firm—Sperry, Zoda & Kane

[57] ABSTRACT

An apparatus for measuring the rheological properties of polymer melts, polymer solutions and other materials including the placement of a specimen of the material to be tested within the intervening space between a forcibly rotatable member and a stationary member both of which have a common axis of symmetry, further including a drive device to forcibly rotate the rotatable member about the common axis of symmetry to shear the specimen, also including the measuring of the force required to shear the specimen, in order to determine the modules of elasticity, yield stress and steady state viscosity of the specimen, further abruptly stopping the rotation of the forcibly rotated member and measuring the stress relaxation of the specimen as a function of time, or alternatively, releasing the forcibly rotated member and measuring the recoverable strain and rate of strain recovery as a function of time for the purpose of determining the elastic properties of the specimen, and further including an alignment bearing device such that the axis of rotation of the rotatable member is co-axial with the stationary member and further bearing device consisting of axially located small diameter pins rigidly fixed to and protruding from the stationary member and the main frame of the apparatus into axially located holes in the other members to maintain co-axial rotation with very low frictional resistance to the relative rotation of the rotatable and non-rotatable members.

10 Claims, 1 Drawing Sheet

U.S. Patent     Aug. 2, 1988     4,760,734
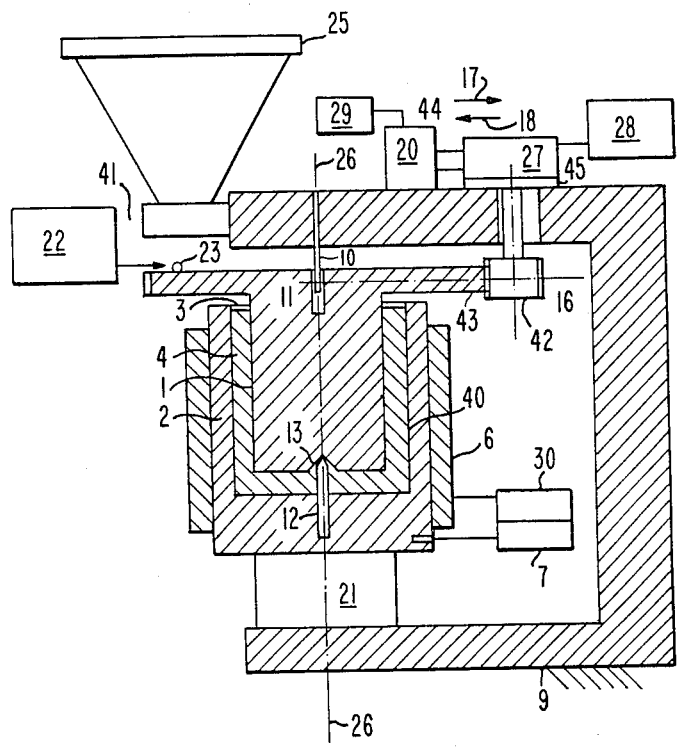

APPARATUS FOR MEASURING THE RHEOLOGICAL PROPERTIES OF MATERIALS

This application is a continuation-in-part of U.S. Ser. No. 826,955 filed Feb. 7, 1986, now abandoned.

BACKGROUND OF THE INVENTION

1. Field of the Invention

Rheology is defined as the science of the flow and deformation of matter. Some materials approach the behavior of ideal fluids and are described as being viscous. Other materials approach the behavior of ideal solids and are described as being elastic. Most materials exhibit a combination of viscous and elastic behavior and are described as being viscoelastic. The viscoelastic behavior of materials is important in both the processing of materials and application of materials.

For example, a polymer material to be processed is put into a fluid state either by the application of heat or by dissolving it in a low molecular weight solvent to form a solution. The resulting fluid is of a viscoelastic nature and may be formed into a fabricated shape either by flow under the force of gravity or by flow under an externally applied pressure. In order to properly design such processing operations and the equipment associated therewith it is important to have accurate measurements of the rheological behavior of the viscoelastic polymer melt or solution.

It is also important to have accurate measurements of the rheological properties of materials other than polymers such as inks, colloidal suspensions, copying toners, etc. The usefulness of these materials is greatly dependent on their rheological characteristics. Customer acceptance of foods such as mayonaise, puddings, and bread doughs are dependent on their rheology, as well as tooth pastes and cosmetics.

2. Description of the Prior Art

There is a large amount of prior art dealing with rotational rheometers. These take many forms. For example, U.S. Pat. No. 3,680,366 discloses a torsional operating device which does not measure the recoverable strain of the material tested, an important objective of the present invention. Similarly Masashi Umeno et al in U.S. Pat. No. 3,479,858 discloses a torsional oscillating device for measuring viscoelasticity but this system does not measure elasticity or recoverable strain, an important feature of the present invention.

U.S. Pat. No. 2,484,761 shows strain gauges attached to an arm to measure stress. Although this system might be used with the apparatus based on the present invention it does not measure recoverable strain.

Maxwell in U.S. Pat. No. 4,092,849 discloses an apparatus very similar in design and objective to the present invention but the bearing system therein is made up of conventional ball bearings which have the undesirable features of being difficult to align, as well as being higher than desired in friction and requiring constant cleaning to produce reliable results. The objective of the present invention is to overcome these undesirable characteristics by providing an improved bearing system that insures alignment and minimal friction.

U.S. Pat. No. 4,566,324 describes a rotational rheometer of quite conventional geometry with an elaborate radiation double refraction system for measuring specimen deformation. The present invention does not involve any such system. This apparatus does not measure recoverable strain.

Garritano in U.S. Pat. No. 4,601,195 discloses a device for measuring the viscoelastic properties of materials which is perported to measure both the viscous and elastic properties. The elastic properties are assumed to be proportional to the normal force or "Weissenberg Effect". The present invention does not use this or any other assumption but rather measures the elastic properties directly by measuring the recoverable strain. The Garritano apparatus does not do this. The two systems operate on entirely different principles.

Myerholtz in U.S. Pat. No. 3,277,700 presents an improved torsional pendulum. This produces an oscillatory signal to indicate the properties of the specimen. This principal is not used in the present invention.

Zemp et al in U.S. Pat. No. 3,545,257 describes a rotational viscometer for measuring the viscosity of materials in which a hydrostatic support means is used to provide a low friction bearing. This is not the system of the present invention. The Zemp apparatus does not attempt to measure elasticity of recoverable strain.

SU Patent No. 1111072-A presents a rotating viscometer with bearing means consisting of pins protruding axially from both ends of the central cylindrical member. This is exactly the opposite to the present invention. If these pins of this patent become bent, then the control cylindrical member will not rotate about its axis of symmetry but rather will wobble. The apparatus of SU No. 1111072-A does not measure elasticity or recoverable strain.

WO Patent No. 86/00408 describes a rotation viscometer with an electromagnetic system for detection of the motion of the inner cylindrical member. The upper bearing consists of a pin protruding axially from the rotating member. This is exactly the opposite to the present invention and suffers from the same undesirable characteristics as SU No. 1111072-A.

SU Patent No. 1062-565-A describes a normal stress meter in which the bearing system consists of pins protruding axially inward from the frame to ball bearings in the ends of the rotating member. This patent differs particularly from the present invention since the ball bearings are higher in friction than the system presently disclosed. Also ball bearings need lubrication and cleaning. The system of the present invention does not.

Finally since the test measurements are made at various temperatures the system of SU No. 1062-565-A has a very serious defect. With an increase in temperature the rotating member expands axially. This produces an increasingly strong axial force on the bearing due to the tapered pin and ball bearing configuration. This produces a large increase in friction and it may even be possible to freeze the bearings with this system. The present invention overcomes this problem by allowing the rotating member to expand freely.

The current apparatus for measuring rheological properties have been reviewed in detail in (1) Rheometers for Molten Plastics by John M. Dealey, published by Van Nostrand Reinhold Co. The final paragraph of this book points out that a need definitely exists for an inexpensive rheometer capable of measuring rheological characteristics including elasticity. It is an important object of the present invention to satisfy this need.

Past efforts in devising apparatus for the measurement of rheological properties have resulted in complex and expensive apparatus requiring extensive data reduction.

One attempt to devise a rheometer to measure elastic recoverable strain is disclosed in U.S. Pat. No. 4,092,849 granted to the present inventor. This apparatus is marketed under the name of Melt Elasticity Tester and is discussed by Dealey in the above reference. He describes the principal of operation as simple and straight forward but mentions difficulty in loading the specimen in the apparatus. He also describes the bearings used to hold the rotatable members coaxially aligned as requiring careful attention. It is an important objective of the present invention to overcome this problem.

It is well known that any rheometer used to measure the specimens elastic recoverable strain characteristics must be as close to friction free as is physically possible. This has led in the past to the use of air bearings to support the rotatable members, but it has been found that all such bearings include residual torque, which increases the difficulty in interpreting the data. Also, air bearings are expensive to manufacture and require a supply of ultra pure air for operation.

The present invention overcomes many of the undesirable features of previous rheometers due to the simple construction of the almost friction free coaxially aligning bearings.

SUMMARY OF THE INVENTION

The present invention includes a specimen holding space located between two coaxial members. One member is forcibly rotated by a drive means to accomplish shearing of the specimen while the other member is prevented from rotating by a torque measuring device thereby measuring the torque required to accomplish shearing and thereby further determining the stress vs strain characteristics from which the modules of elasticity yield stress and steady state viscosity may be calculated. The forcibly rotated member can then be forcibly stopped to measure the decay of torque as a function of time from which the stress relaxation characteristics may be determined. Alternatively, the forcibly rotated member may be released from the drive means and the rotation of the released member followed as a function of time to measure the rate of strain recovery and the total amount of recoverable strain.

The two members are held in coaxially rotatable position with respect to one another by means of two axially located small diameter pins one of which is securely fixed at the axis of symmetry of the non-rotatable member and protrudes therefrom into an axially located conical hole in the other member. The other pin is securely fixed to the main frame of the apparatus and protrudes into an axially located hole in the forcibly driven rotatable member at the opposite axial end from the other pin.

A principle of the present invention is the discovery that such a bearing support system assures that the member rotationally driven always rotates about its axis of symmetry during the shearing experience and, similarly, always rotates about its axis of symmetry when released to rotate in accordance with the recoverable elastic strain in the specimen. It has been further shown that such a bearing support system is strong enough and rigid enough to be used in a rheometer for the study of polymer melts and is very low in friction thereby permitting measurements of great accuracy.

It is an object of the present invention to provide an improved apparatus for measuring the rheological properties of materials which is relatively uncomplicated.

It is an object of the present invention to provide an improved apparatus for measuring the rheological properties of materials which is relatively easy to manufacture.

It is an object of the present invention to provide an improved apparatus for measuring rheological properties of materials which can be operated by very simple procedures.

It is an object of the present invention to provide an improved apparatus for measuring the rheological properties of materials which is relatively simple to maintain.

It is an object of the present invention to provide an improved apparatus for measuring the rheological properties of materials which make use of inexpensive alignment bearings.

It is an object of the present invention to provide an improved apparatus for measuring the rheological properties of materials which include alignment bearings having very low friction coefficient.

It is an object of the present invention to provide an improved apparatus for measuring the rheological properties of materials which is usable to specifically measure modulus of elasticity, yield stress, steady-state viscosity, stress relaxation, recoverable strain and rate of strain recovery in a relatively friction-free environment.

It is an object of the present invention to provide an improved apparatus for measuring the rheological properties of materials which include an angular position monitoring system to provide data on relative movement of two co-axially relatively rotatable members.

It is an object of the present invention to provide an improved apparatus for measuring the rheological properties of materials which include pin bearing means for maintaining rotational alignment between a power-driven member and a fixed member.

It is an object of the present invention to provide an improved apparatus for measuring the rheological properties of materials which include pin bearing means for maintaining alignment between a rotational member and a frame means thereoaround.

It is an object of the present invention to provide an improved apparatus for measuring the rheological properties of materials which includes a temperature control means for maintaining the specimen at a predetermined desired steady-state temperature.

BRIEF DESCRIPTION OF THE DRAWING

While the invention is particularly pointed out and distinctly claimed in the concluding portions herein, a preferred embodiment is set forth in the following detailed description which may be best understood when read in connection with the accompanying drawing, in which:

The FIGURE is an axial sectional view of a preferred embodiment of the present invention.

DETAILED DESCRIPTION OF THE PREFERRED EMBODIMENT

As shown in the FIGURE an essentially cylindrical first member 1 is centrally located within the cylindrical hollow bore 40 of a second member 2 to provide an intervening space 3, which is essentially annular, therebetween to hold the specimen 4 to be tested. Conventional rotational drive means 27 is provided to rotate member 1 through pinions 42 and 43 about axis of rotation 26. Conventional heating means such as electric resistance heater 6 can be operated in conjunction with a temperature controlling device 30 and a measuring device such as a thermocouple 7 to bring the specimen 4 to the desired test temperature. Member 2 is mounted on a conventional torque measuring transducer 21 which is mounted in the main frame 9. Transducer 21 may be of any nature commonly available in the instrumentation field.

Member 1 is mounted in a pair of very low friction bearings so that it may freely rotate about axis 26. The upper bearing consists of a pin 10 rigidly mounted in frame 9 and extending into an axial cylindrical hole 11 in member 1. The internal diameter of the hole 11 is slightly larger than the external diameter of the pin 10 thereby providing a small clearance. Pin 10 does not extend to the bottom of hole 11 thereby preventing any vertical action or reaction in this upper bearing system. This allows member 1 to thermally expand axially as the specimen 4 is heated to the test temperature.

The lower bearing consists of a pointed pin 12 rigidly mounted in member 2 on axis 26 and extending into a conicial, axial hole 13 in member 1 thereby providing a point contact between the tip of pin 12 and the conical end of hole 13 on axis 26. The weight of member 1 is supported on this point contact.

A release is provided. For example, an electromagnetic lateral drive means 20 or other suitable lateral drive means is attached to frame 9. Activation of said drive means causes rod 44 to push against drive means 27 which is mounted on slides 45 causing drive means 27 to move in direction 17 thereby separating pinion 42 from pinion 43 along axis 16 thereby releasing member 1 to rotate freely about axis 26. For the next test, pinion 42 will again engage pinion 43 upon deactivation of drive means 20 and movement of drive means 27 in drection 18.

In addition an angular position monitoring system 41 is provided. An example of such a system consists of an intermittent timed light source 22, such as a strobe means shining on a hemispherical reflector 23 attached to member 1. The light reflected by reflector 23 enters the lens of recording means such as camera 25 and is recorded on the camera's film in accordance with the angular position of element 1 and the timing of the intermittent light thereby providing a record of the rotation of element 1 as a function of time. Another example of an angular position monitoring system would be the fiber optics system disclosed in U.S. Pat. No. 4,092,849. There are many other specific angular position monitoring systems or optical encoders usable with the present invention. The angular position monitoring system may be of any nature commonly available in the instrumentation field.

The procedure of measurement includes insertion of a specimen 4 of the material to be tested for its rheological properties in the annular space 3 to be brought to the desired steady-state test temperature by heating of member 2 through control in any conventional manner in conjunction with heating means 6 and thermocouple 7. Once temperature equlibrium has been established, drive means 27 rotates member 1. During this shearing the force required to accomplish the shearing is measured by the transducer gauge 21 and may be recorded by any conventional means. From this record the rheological characteristics of stress vs strain, modulus, yield stress and viscosity may be calculated.

When the desired amount of shearing has taken place the drive means may be stopped by a stop means 28 which could be a limit switch or other conventional means thereby stopping the rotation of member 1. Concurrently with the cessation of shearing the electromagnet lateral drive means may be activated by any conventional means such as a switch means 29 associated electrically with the method of stopping the shearing. The activation of the electromagnetic 20 causes the rod 44 to move in the direction 17 thereby disengaging pinions 43 and 42 and allowing the stored elastic strain in the specimen 4 to cause the member 1 to rotate about axis 26 at a rate and magnitude directly related to the rate of recovery of strain and the the magnitude of the recoverable strain stored in the specimen 4 as a result of the previous shearing imparted by the drive means. Because the forces associated with recoverable strain are very small it is essential that member 1 be mounted in bearings which have an absolute minimum of friction.

As the strain recovery takes place the motion of element 1 is recorded by the angular position monitoring system 41. From this record, the rheological properties of elasticity or rate of strain recovery and total magnitude of recoverable strain may be calculated.

An alternative procedure of measurement may be used wherein the specimen 4 may be sheared as described above but when the desired amount of shearing has taken place the drive means will be stopped as described above. However, electromagnet drive means 20 will not be activated to release element 1. This will allow transducer gauge 21 to measure the decay of force exerted by the specimen on member 1 as the specimen relaxes from the previusly applied shearing. From the recorded output of the transducer 21 and rheological property of time dependent stress relaxation may be calculated.

It can therefore be seen that the rheological properties of materials can be measured by this improved apparatus as disclosed herein which is uncomplicated and provides ease of manufacture, maintenance and operation, in addition to providing a bearing system for support of the rotating member 1 which is very simple and inexpensive to manufacture and yet extremely low in friction.

To demonstrate the low friction of this bearing system the following experiment was performed. A specimen of 400,000 weight average molecular weight polystyrene was placed in the apparatus and heated to 205° C. After thermal equilibrium was attained the specimen was sheared as described above. After the shearing was stopped the electromagnetic drive means 20 was not activated and the stress was allowed to relax to 20% of its original value. This took about 100 seconds. At this point in time the electromagnetic drive means 20 was activated and rotation of element 1 in response to the stored recoverable strain was monitored by the angular position monitoring system. The element 1 rotated slowly as the strain recovered. The amazing observation was that even after 100 seconds of stress relaxation the recoverable strain rotation continued through 6000 seconds (1.7 hrs.) at the extremely low rate of 0.0000637 revolutions per minute (this corresponds to a recoverable strain recovery rate of 0.0002 strain units per second). This experiment clearly demonstrates that the bearing system of the present invention is extremely low in friction and is very well suited for use in rheological measurements.

It should be noted that bearing systems somewhat similar to that described above to support element 1 have been used for other applications in the past. For example many of the gears and cogs in watches and clocks have pins extending axially which fit into small holes or jewels to give low friction bearings. The present invention differs from these examples in an important aspect. If during either construction or use a pin is misaligned or bent in any system where the pins extend outward from the element being supported, then the element will not rotate about its axis of symmetry. On the other hand, in the present invention even if a pin is misaligned or bent, the element being supported will still rotate about its axis of symmetry because the holes into which the pins fit are defined on the axis of symmetry.

It should also be further noted that the pinions 42 and 43 and the upper bearing system 10 and 11 all lie along a straight line, that is axis 16. This means that during the shearing part of the experiment all the forces resulting from the shearing are supported by the upper bearing system and therefore there is not lateral or sideways force on the lower bearing pin 12. This important aspect of the present invention prevents damage to the point of pin 12.

While particular embodiments of this invention have been shown in the drawing and described above, it will be apparent, that many changes may be made in the form, arrangement and positioning of the various elements of the combination. In consideration thereof it should be understood that preferred embodiments of this invention disclosed herein are intended to be illustrative only and not intended to limit the scope of the invention. For example, elements 1 and 2 may be replaced by other coaxial geometrics such as a cone and plate or two disks with surfaces perpendicular to the axis of rotation 26 or other logical shearing geometries. As such the matter covered in the following claims includes all such modifications and changes as may fall within the entire true spirit and scope of the present invention.

I claim:

1. An improved apparatus for measuring the rheological properties of materials which comprises:
   (a) a frame means;
   (b) a first member mounted for low friction rotation with respect to said frame means, said first member defining an axis extending vertically about which said first member is rotationally movable, said first member defining an upper hole means and a lower hole means therein to facilitate low friction rotation thereof;
   (c) a second member mounted on said frame means about said axis, said second member being positioned adjacent said first member to define therebetween an intervening space to receive therein a specimen of material to be tested;
   (d) a rotational drive means to drive said first member about said axis to allow relative rotational movement between said first member and said second member to cause shearing of the specimen positioned therebetween within said intervening space;
   (e) a releasable retaining means to selectively prevent and permit rotation of said first member;
   (f) a stop means to selectively halt operation of said rotational drive means and stop rotation of said first member;
   (g) an upper bearing means including a generally cylindrical upper pin means of smaller external diameter than said upper hole means, said upper pin means being fixedly secured with respect to said frame means and being positioned co-axially with respect to said vertically extending axis of said first member, said upper pin means extending into said upper hole means defined in said first member to a depth that is substantially less than the depth of said upper hole means to spatially dispose said upper pin means from the bottom of said upper hole means to prevent contact therebetween responsive to said first member being thermally expanded vertically due to being heated to test temperature;
   (h) a lower bearing means including a lower pin means fixedly secured with respect to said second member and extending upwardly therefrom, said lower pin means being positioned co-axially with respect to said vertically extending axis, said lower pin means extending into said lower hole means defined in said first member; and
   (i) an angular position monitoring system for recording the movement of said first member with respect to said frame means.

2. The apparatus as defined in claim 1 further including a torque transducer mounted in said frame means which comprises a torque measuring means to measure and record the force required to prevent rotational movement of said second member.

3. The apparatus as defined in claim 1 wherein said first member is generally cylindrical and wherein said second member defines a cylindrical opening therein into which said first member extends to define said intervening space as the annular region therebetween.

4. The apparatus as defined in claim 1 wherein said lower hole means is conical in cross-section to more effectively receive said lower pin means extending thereinto.

5. The apparatus as defined in claim 4 wherein said lower pin means includes an upwardly extending tip thereon to facilitate retaining of said lower pin means within said conical lower hole means.

6. The apparatus as defined in claim 1 further including a heating means.

7. The apparatus as defined in claim 6 wherein said heating means comprises an electrical resistance heater extending about said second member.

8. The apparatus as defined in claim 6 further including a temperature controlling device for maintaining of the specimen at a desired temperature.

9. The apparatus as defined in claim 1 including a thermocouple means for sensing the temperature of the specimen during experimentation.

10. An improved apparatus for measuring the rheological properties of materials which comprises:
    (a) a frame means including a torque transducer mounted therein;
    (b) a first member being generally cylindrical mounted for low friction rotation with respect to said frame means, said first member defining an axis extending vertically about which said first member is rotationally movable, said first member defining an upper cylindrical hole means and a lower hole means therein to facilitate low friction rotation thereof, said lower hole means being conical in cross-section;
    (c) a second member mounted on said torque transducer on said frame means about said axis, said second member being generally cylindrical, said second member being positioned adjacent said first member to define therebetween an intervening annular space to receive therein a specimen of material to be tested;

(d) a rotational drive means to drive said first member about said axis to allow relative rotational movement between said first member and said second member to cause shearing of the specimen positioned therebetween within said intervening space;
(e) a releasable retaining means to selectively prevent and permit rotation of said first member;
(f) a stop means to selectively halt operation of said rotational drive means and stop rotation of said first member;
(g) an upper bearing means including an upper pin means fixedly secured with respect to said frame means and being positioned co-axially with respect to said vertically extending axis, said upper pin means extending into said upper hole means defined in said first member, said upper pin means having an external diameter smaller than the internal diameter of said upper hole means to facilitate rotation of said first member with respect to said upper bearing means, said upper pin means further having the lower end thereof spatially disposed from the bottom of said upper hole means to prevent a vertical force from being created when said first member expands vertically due to thermal expansion upon being heated to test temperature;
(h) a lower bearing means including a lower pin means fixedly secured with respect to said second member and extending upwardly therefrom, said lower pin means being positioned co-axially with respect to said vertically extending axis, said lower pin means extending into said conical lower hole means defined in said first member, said lower pin means further including an upwardly extending tip thereon to facilitate retaining of said lower pin means within said conical lower hole means;
(i) an angular position monitoring system for recording the movement of said first member with respect to said frame means;
(j) torque measuring means defined within said torque transducer to measure and record the force required to prevent rotational movement of said second member;
(k) a heating means extending about the second member, said heating means comprising an electrical resistance heating member;
(l) a temperature controlling device for maintaining of the specimen at a desired temperature and being operatively connected to said heating means for controlling activation thereof; and
(m) a thermocouple means for sensing the temperature of the specimen during experimentation and providing information to said temperature controlling device for controlling selective operation of said heating means.

* * * * *